US010149803B2

(12) United States Patent
Yang et al.

(10) Patent No.: US 10,149,803 B2
(45) Date of Patent: *Dec. 11, 2018

(54) ANTI-CALCULUS ORAL COMPOSITIONS

(71) Applicant: The Procter & Gamble Company, Cincinnati, OH (US)

(72) Inventors: Hongmei Yang, Beijing (CN); Ross Strand, Singapore (SG); Yang Su, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/736,352

(22) Filed: Jun. 11, 2015

(65) Prior Publication Data
US 2016/0008238 A1    Jan. 14, 2016

(30) Foreign Application Priority Data

Jul. 10, 2014    (WO) ................ PCT/CN2014/081955

(51) Int. Cl.
*A61K 8/24* (2006.01)
*A61K 33/06* (2006.01)
*A61K 8/19* (2006.01)
*A61Q 11/00* (2006.01)
*A61K 8/21* (2006.01)

(52) U.S. Cl.
CPC .................. *A61K 8/24* (2013.01); *A61K 8/19* (2013.01); *A61K 8/21* (2013.01); *A61Q 11/00* (2013.01); *A61K 2800/28* (2013.01); *A61K 2800/592* (2013.01)

(58) Field of Classification Search
CPC . A61Q 11/00; A61K 8/19; A61K 8/24; A61K 33/06
See application file for complete search history.

(56) References Cited

U.S. PATENT DOCUMENTS

| | | | |
|---|---|---|---|
| 4,247,526 A | 1/1981 | Jarvis et al. | |
| 4,684,918 A | 8/1987 | Solomon | |
| 4,923,684 A | 5/1990 | Ibrahim et al. | |
| 4,985,236 A | 1/1991 | Ibrahim et al. | |
| 5,145,667 A | 9/1992 | Ibrahim et al. | |
| 5,176,900 A | 1/1993 | White, Jr. et al. | |
| 5,180,576 A | 1/1993 | Winston et al. | |
| 5,599,527 A | 2/1997 | Hsu et al. | |
| 5,730,959 A | 3/1998 | Prencipe et al. | |
| 2003/0072721 A1* | 4/2003 | Riley ................ | A61K 8/19 424/49 |
| 2007/0009447 A1* | 1/2007 | Gadkari ............ | A61K 8/19 424/49 |
| 2009/0269284 A1 | 10/2009 | Sickma et al. | |

FOREIGN PATENT DOCUMENTS

| | | |
|---|---|---|
| CN | 1044224 A | 8/1990 |
| EP | 0219483 A2 | 4/1987 |
| EP | 0236290 A1 | 9/1987 |
| EP | 2415473 A1 | 2/2012 |
| GB | 1132830 | * 11/1968 |
| KR | 2002/0054045 A | 7/2002 |
| WO | WO 2000/62749 A1 | 10/2000 |
| WO | WO 0245677 A1 | 6/2002 |
| WO | WO2012044785 A2 | 4/2012 |
| WO | WO2013034421 A2 | 3/2013 |

OTHER PUBLICATIONS

International Search Report for PCT/CN2014/081955 dated Aug. 10, 2016.

* cited by examiner

*Primary Examiner* — Lezah Roberts
(74) *Attorney, Agent, or Firm* — Parker D. McCrary; Alexandra S. Anoff

(57) ABSTRACT

The present invention provides an oral composition comprising: (a) from 1 wt % to 60 wt % of a calcium-containing abrasive; (b) a calcium-catching phosphate source in an amount sufficient to provide at least 100 mM of phosphate ions, $PO_4^{3-}$; (c) no more than 20 wt % of a humectant; and (d) at least 5 wt % of water; wherein the oral composition has a pH from 8 to 11.

17 Claims, No Drawings

ANTI-CALCULUS ORAL COMPOSITIONS

CROSS REFERENCE TO RELATED APPLICATION

This Application claims the benefit of Application Serial No. CN2014/081955 filed Jul. 10, 2014.

FIELD OF THE INVENTION

The present invention relates to anti-calculus oral compositions comprising a calcium-containing abrasive.

BACKGROUND OF THE INVENTION

Dental calculus, or tartar as it is sometimes called, is a deposit which forms on the surfaces of teeth at the gingival margin. Supragingival calculus appears principally in the areas near the orifices of the salivary ducts; e.g., on the lingual surfaces of the lower anterior teeth and on buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of micro-organisms.

As the mature calculus develops, its appearance becomes visibly white or yellowish in color unless stained or discolored by some extraneous agent. This is undesirable from an aesthetic standpoint. One way to address the problem is with routine dental visits to mechanically remove the calculus deposits. Another solution is through the use of a variety of chemical and biological agents to retard calculus formation or to remove calculus after its formation.

The latter approach to chemically inhibit calculus formation generally involves chelation of calcium ion and/or crystal growth inhibition. This approach prevents the calculus from forming and/or breaks down mature calculus through the removal of calcium. There are a number of chelating agents that are well-known as being effective for this purpose, such as for example, pyrophosphate salts and polyphosphates.

Silica is a commonly used abrasive in oral care compositions. Calcium containing abrasives have also been used in oral compositions (e.g., toothpastes). However, the problem with calcium containing abrasives is that the calcium ions will complex with free pyrophosphate or phosphate ions and other anti-calculus sources in the oral compositions, leading to a potential decrease in anti-calculus efficacy. As a result, calcium containing abrasives, such as for example calcium carbonate, are not preferred abrasives in anti-calculus oral compositions.

Thus, there is a need for an oral composition with improved anti-calculus efficacy. It is desirable that the oral composition provides improved cleaning efficacy.

SUMMARY OF THE INVENTION

In one aspect, the present invention provides an oral composition comprising:
(a) from 1 wt % to 60 wt % of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite and combinations thereof;
(b) a calcium-catching phosphate source in an amount sufficient to provide at least 100 mM of phosphate ions, $PO_4^{3-}$;
(c) no more than 20 wt % of a humectant; and
(d) at least 5 wt % of water;
wherein the oral composition has a pH from 8 to 11.

In another aspect, the present invention provides a method of controlling dental calculus, comprising the step of administering to a subject's oral cavity an oral composition of the present invention.

In yet another aspect, the present invention provides the use of a calcium-catching phosphate source for manufacturing an anti-calculus oral composition, wherein the anti-calculus oral composition comprises a calcium-containing abrasive and has a pH from 8 to 11, and wherein the calcium-catching phosphate source is present in an amount sufficient to provide at least 100 mM of phosphate ions, $PO_4^{3-}$, in the anti-calculus oral composition.

It is generally believed that the calcium-catching phosphate source should be sufficiently soluble, and bio-available, to provide sufficient anti-calculus efficacy in the presence of a calcium-containing abrasive. However, based on a pH triggered effect, the present invention provides an anti-calculus oral composition even though there is a very low concentration of soluble calcium-catching phosphate source available in the oral composition. According to the present invention, high pH deactivates the calcium-catching phosphate source as a non-efficacious insoluble source when the oral composition is on shelf, but at point of use, the shift in pH forms phosphate species that allow the capture of additional calcium or calcium ions and thus provide an anti-calculus benefit.

These and other features, aspects, and advantages of the present invention will become evident to those skilled in the art from the detailed description which follows.

DETAILED DESCRIPTION OF THE INVENTION

Definitions

The term "oral composition" as used herein means a product that in the ordinary course of usage is retained in the oral cavity for a time sufficient to contact some or all of the dental surfaces and/or oral tissues for purposes of oral activity. In one embodiment, the composition is an "oral care composition" meaning that the composition provides a benefit when used in the oral cavity. The oral composition of the present invention may be in various forms including toothpaste, dentifrice, tooth gel, tooth powders, tablets, rinse, sub gingival gel, foam, mousse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

The terms "tartar" and "calculus" are used interchangeably herein and refer to mineralized dental plaque biofilms.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

All measurements referred to herein are made at room temperature of about 25° C., unless otherwise specified.

Calcium-Containing Abrasive

Oral compositions, especially in the form of toothpaste, gel, or powder, generally contain an abrasive. Gels usually contain silica, whereas opaque creams generally contain calcium-containing abrasives.

The oral compositions of the present invention comprise from 1 wt % to 60 wt % of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite and combinations thereof. In a preferred embodiment, the oral composition comprises from 5 wt %, 10 wt %, 15 wt %, 20 wt % or 25 wt % to 35 wt %, 40 wt %, 50 wt %, 55 wt % or 60 wt % of the calcium-containing abrasives.

In a preferred embodiment, the calcium-containing abrasive is selected from the group consisting of fine ground natural chalk, ground calcium carbonate, precipitated calcium carbonate and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in PCT Publication No. WO 03/030850 having a medium particle size of 1 to 15 μm and a BET surface area of 0.5 to 3 m$^2$/g. The natural calcium carbonate may have a particle size of 325 to 800 mesh, alternatively a mess selected from 325, 400 600, 800 or combinations thereof; alternatively the particle is from 0.1 to 30 microns, or from 0.1 to 20 microns, or from 5 to 20 microns.

In addition to the calcium-containing abrasive, other abrasives may also be used in the present oral composition depending on the intended degree of abrasion. These include synthetic abrasive polishing agents such as amorphous precipitated silica and silica gels. Other abrasive agents include magnesium carbonate, sodium metaphosphate, potassium metaphosphate, zirconium silicate, potassium metaphosphate, magnesium orthophosphate, tricalcium phosphate, magnesium orthophosphate, trimagnesium phosphate, aluminum silicate, zirconium silicate and perlite.

Calcium-Catching Phosphate Source

The terms "calcium-catching", "calcium-chelating", and "calcium-binding" are used interchangeably herein, and refer to the capability of attaching to calcium or calcium ions chemically or physically. Preferably, the calcium-catching phosphate source used herein is a phosphate source having two or more phosphate groups so as to chelate calcium ions. In an oral care composition, the calcium-catching phosphate source can be used as an anti-calculus agent, preventing calculus formation.

The formation of dental calculus occurs as a result of mineralization of the plaque by the saliva, whereby the calcium and phosphate from the saliva deposit and accumulates on the plaque. The use of a calcium-catching phosphate source acts as a crystal growth inhibitor to limit both the mineralization of the plaque and subsequent tartar build up. Within an oral composition comprising a calcium-containing abrasive, the calcium-catching phosphate source binds to the free calcium within the oral composition, forming an insoluble calcium-phosphate complex, that is unable to further bind with calcium so as to inhibit the crystal growth and provide anti-calculus benefit. Based on clinically proven anti-tartar toothpastes, a high level of available calcium-catching phosphate source is required. Therefore, it is generally believed that the calcium-catching phosphate source will not be able to provide sufficient anti-calculus efficacy in the presence of a calcium-containing abrasive. However, the present inventors surprisingly found that anti-calculus efficacy can be achieved if the calcium-catching phosphate source, either in a soluble form or in an insoluble form, provides at least 100 mM of phosphate ions, $PO_4^{3-}$. The units "mM" and "mmol/L" are used interchangeably herein, and refer to the molar concentration of phosphate ions, $PO_4^{3-}$, in the oral composition.

In an embodiment, the amount of the calcium-catching phosphate source in the oral composition is sufficient to provide at least 120 mM, preferably from 140 mM, 200 mM, 300 mM, or 400 mM to 500 mM, 600 mM, 800 mM or 1000 mM of phosphate ions, $PO_4^{3-}$.

Preferred calcium-catching phosphate sources include pyrophosphate sources, polyphosphate sources, polyphosphorylated inositol sources, polyphosphonate sources, or combinations thereof. The calcium-catching phosphate sources may be present singularly or in combination with additional anti-calculus agents.

Pyrophosphate Source

The pyrophosphate sources useful in the present invention include dialkali metal pyrophosphate salts, tetra alkali metal pyrophosphate salts, and combinations thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In oral compositions of the present invention, the pyrophosphate source may be present in one of three ways: predominately dissolved, predominately undissolved, or a mixture of dissolved and undissolved pyrophosphate.

Oral compositions comprising predominately dissolved pyrophosphate refer to oral compositions where at least one pyrophosphate ion source is in an amount sufficient to provide at least 1.0 wt % free pyrophosphate ions. The amount of free pyrophosphate ions may be present from 1 wt %, 1.5 wt %, 2 wt %, or 3 wt % to 5 wt %, 6 wt %, 10 wt %, or 15 wt %. Free pyrophosphate ions may be present in a variety of protonated states depending on the pH of the composition. In specific embodiments, the amount of Na$_2$H$_2$P$_2$O$_7$, which is preferably used in the oral composition, is present from 0.5 wt % to 13.8 wt % and Na$_4$P$_2$O$_7$ is present from 0.5 wt % to 6 wt % (all are in the unhydrated form). In an alternative embodiment, the amount of Na$_2$H$_2$P$_2$O$_7$ is present from wt1%, 1.5 wt %, 3 wt %, or 4 wt % to 5 wt %, 6 wt %, 8 wt %, or 10 wt %. In another alternative embodiment, the amount of Na$_4$P$_2$O$_7$ is present from 1 wt % or 2 wt % to 3 wt % or 5 wt %.

Oral compositions comprising predominately undissolved pyrophosphate refer to oral compositions containing no more than 20 wt % of the total pyrophosphate salt dissolved in the composition, preferably less than 15 wt %, or more preferably less than 10 wt % of the total pyrophosphate dissolved in the oral composition. Tetrasodium pyrophosphate salt is a preferred pyrophosphate salt in these oral compositions. Tetrasodium pyrophosphate may be the anhydrous salt form or the decahydrate form, or any other species stable in solid form in the oral compositions. The salt is in its solid particle form, which may be its crystalline and/or amorphous state, with the particle size of the salt preferably being small enough to be aesthetically acceptable and readily soluble during use. The amount of pyrophosphate salt useful in making these oral compositions is any tartar control effective amount, and is generally present from 1.5 wt %, 2 wt %, 2.5 wt %, 3.5 wt % or 5 wt % to 6 wt %, 7 wt %, 8 wt %, 10 wt % or 15 wt %.

Oral compositions may also comprise a mixture of dissolved and undissolved pyrophosphate salts. Any of the above mentioned pyrophosphate salts may be used.

Polyphosphate Source

As discussed herein, the polyphosphate sources useful in the present invention include those having three or more phosphate molecules arranged in a linear and/or cyclic configuration. The preferred inorganic polyphosphate salts include tripolyphosphate, tetrapolyphosphate, and hexametaphosphate in a linear and/or cyclic configuration. Polyphosphates larger than tetrapolyphosphate usually occur as amorphous glassy materials. Preferred in this invention are the linear "glassy" polyphosphates having the formula:

wherein "X" is sodium or potassium and "n" averages an integer from 3 to 125, preferably from 6 to 21. Preferred are polyphosphates commercially known as Sodaphos® (n is about 6), Hexaphos® (n is about 13), and Glass H® (n is about 21), which are manufactured by FMC Corporation and Astaris. These polyphosphates may be used alone or in combination.

The polyphosphate source will typically be present from 0.5 wt %, 2 wt %, 4 wt %, 6 wt %, or 7 wt % to 9 wt %, 10 wt %, 12 wt %, 15 wt % or 20 wt %.

Polyphosphorylated Inositol Source

The polyphosphorylated inositol sources useful in the present invention include phytic acid, myo-inositol pentakis (dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis(dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The polyphosphorylated inositol sources will typically be present from 0.1 wt % to 35 wt %, preferably from 2 wt %, 5 wt %, 6 wt % or 10 wt % to 15 wt %, 20 wt %, 25 wt % or 30 wt %. In an alternative embodiment, the polyphosphorylated inositol sources is present from 1 wt % to 9 wt %, or 7 wt % to 12 wt %, or 16 wt % to 28 wt %, or combinations thereof.

Polyphosphonate Source

Polyphosphonates, as used herein, include diphosphonates, polydiphosphonates, and polyphosphonates. Use of these materials can be as their acids or water-soluble salts. Also applicable are synthetic polymers based upon phosphonates, including polymers of diphosphonic acids and polyphosphonic acids. Phosphonates are compounds characterized as containing a covalent P—C bond, which links the phosphate group to a molecule. Diphosphonates are characterized as containing a P—C—P bond. Preferred diphosphonates include azacycloalkane diphosphonates. The synthesis of these materials is described in U.S. Pat. No. 3,941,772 issued Mar. 2, 1976 to Ploger et al. The sodium salts of azacycloheptylidne-2,2-diphosphonic acid (AHP) and ethane-1-hydroxy-1,1-diphosphonate (EHDP) are preferred. A further description of polyphosphonates is found in U.S. Pat. No. 5,338,537, issued Aug. 16, 1994 to White, Jr. et al., and U.S. Pat. No. 3,678,154, issued Jul. 18, 1972 to Widder et al.

The polyphosphonate may be present in an amount from 0.1 wt %, 0.3 wt %, 0.5 wt % or 0.8 wt % to 1 wt %, 2 wt %, 6 wt % or 12 wt %.

Water

The oral compositions of the present invention comprise herein from at least 5 wt %, preferably from 10 wt %, 20 wt %, 30 wt %, or 40 wt % to 60 wt %, 65 wt %, 70 wt % or 80 wt % of total water. In an embodiment, the amount of water present in the composition is from 5 wt % to 20 wt %, or 15 wt % to 38 wt %, or 35 wt % to 50 wt %, or 45 wt % to 68 wt %, or combinations thereof. The water may be added to the formulation and/or may come into the composition from the inclusion of other ingredients. Preferably the water is USP water.

Sweetener

The oral compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the oral composition, alternatively 0.01% to 1%, alternatively from 0.1% to 0.5%, alternatively combinations thereof.

Fluoride Ion Source

The oral compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the oral composition, alternatively from about 0.005% to about 2.0% by weight of the oral composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, zinc fluoride and combinations thereof. In one embodiment, the oral composition contains a fluoride source selected from stannous fluoride, sodium fluoride, and mixtures thereof. In a preferred embodiment of the present invention, the fluoride ion source is sodium monofluorophosphate, and wherein the oral composition more preferably comprises 0.0025% to 2% of the sodium monofluorophosphate by weight of the oral composition, alternatively from 0.5% to 1.5%, alternatively from 0.6% to 1.7%, alternatively combinations thereof. In one embodiment, the oral composition comprises from 1 parts per million (ppm) to 15,000 ppm, alternatively from 100 ppm to 8,000 ppm, alternatively from 5,000 ppm to 10,000 ppm, alternatively from 7,000 to 9,000 ppm, of monofluorphosphate (MFP) ion.

pH

The pH of the present oral composition is preferably in the range of 8 to 11, alternatively 8.0, 8.5, 9.0 or 9.5 to 10.5, 10.7, 11.0 or 11.3.

The pH is preferably achieved through a proper balancing of the calcium-catching phosphate sources or by addition of an alkaline or acidic agent. The high pH is believed to stabilize the binding of the calcium-containing abrasive and the calcium-catching phosphate source, which creates an insoluble calcium-phosphate complex, e.g., calcium-phosphate oxide/hydroxide species. Upon a change in pH, the insoluble calcium-phosphate complex tends to form different phosphate species that allow the capture of additional calcium ions and thus provide an anti-calculus benefit.

It is desirable for the compositions of the present invention to remain at a basic pH before being dispensed, but then to relatively quickly change pH to an acidic level (i.e., below 7) upon application to the oral cavity. In an alternative embodiment, a high water content of the inventive oral composition is believed to facilitate more rapid pH reduction of the composition when exposed to the low pH environment of the oral cavity, thereby enabling the formation of the different phosphate species that allow the capture of additional calcium ions. This is important since oral compositions are generally not contained in oral cavities for a prolonged period of time and thus the pH change from basic to acidic is expected to happen in a relatively short amount of time.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in use, the electrode is kept immersed in a pH 7 buffer solution or an appropriate electrode storage solution.

pH Modifying Agent

The oral compositions herein may include an effective amount of a pH modifying agent, alternatively wherein the pH modifying agent is a pH buffering agent. pH modifying agents, as used herein, refer to agents that can be used to adjust the pH of the oral compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, orphosphoric acid. In one embodiment, from 0.01% to 3%, preferably from 0.1% to 1%, of TSP by weight of the oral composition, and 0.001% to 2%, preferably from 0.01% to 0.3% of monosodium phosphate by weight of the oral composition is used. Without wishing to be bound by theory, TSP and monosodium phosphate may also have calcium ion chelating activity and therefore provide some monofluorophosphate stabilization (in those formulations containing monoflurophospahte).

Surfactant

The oral compositions herein may include a surfactant. The surfactant may be selected from anionic, nonionic, amphoteric, zwitterionic, cationic surfactants, or mixtures thereof. The oral composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total oral composition. Non-limiting examples of anionic surfactants may include those described at U.S. Patent Appl. Publication No. US2012/0082630A1 at paragraphs 32, 33, 34, and 35. Non-limiting examples of zwitterionic or amphoteric surfactants may include those described at U.S. Patent Appl. Publication No. US 2012/0082630A1 at paragraph 36; cationic surfactants may include those described at paragraphs 37 of the reference; and nonionic surfactants may include those described at paragraph 38 of the reference. In one embodiment, the oral composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the oral composition.

Thickening Agent

The oral compositions herein may include one or more thickening agents. A thickening agent may be used in an amount from 0.01 wt % to 20 wt %, or from 0.01 wt %, 0.1 wt % or 0.3 wt % to 3 wt %, 10 wt % or 20 wt %, or from 0.1 wt % to 5 wt %. Non-limiting examples may include those described in US 2008/0081023A1 at paragraphs 134 to 137, and the references cited therein.

In one embodiment, the thickening agents is selected from the group consisting of xanthan gum, cellulosic polymer, carrageenan, polyacrylic acid, cross-linked polyacrylic acid, polycarbophil, alginate, clay, glucose, pectin, gelatin, and combinations thereof.

In another embodiment, the oral composition comprises a linear sulfated polysaccharide as a thickening agent. Carrageenans or carrageenins are one example of a linear sulfated polysaccharide. Generally, carrageenans can vary based upon the degree of sulfation that includes: Kappa-carrageenan, Iota-carrageenan, and Lambda-carrageenan. Combinations of carrageenans can be used. In one embodiment, the composition contains from 0.1% to 3%, of a linear sulfated polysaccharides by weight of the composition, preferably from 0.5% to 2%, alternatively from 0.6% to 1.8%, alternatively combinations thereof. In one embodiment, Iota-carrageenan is used.

In another embodiment, the oral composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In another embodiment, the oral composition comprises from 0.5% to 5% by weight of the composition of a silica agent, preferably from 1% to 4%, alternatively from 1.5% to 3.5%, alternatively from 2% to 3%, alternatively from 2% to 5% alternatively from 1% to 3%, alternatively combinations thereof.

In another embodiment, the oral composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A). In one embodiment, the oral composition contains from 0.1% to 3% of a CMC by weight of the oral composition, preferably from 0.5% to 2%, alternatively from 0.6% to 1.8%, or alternatively combinations thereof.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the oral composition comprises a thickener comprising: (a) 0.01% to less than 1.4%, preferably from 0.1% to 1.3%, more preferably from 0.5% to 1.3% of a carrageenan by weight of the oral composition; and (d) greater than 0.4 wt % to 2 wt %, preferably from 0.5% to 1.8%, more preferably from 0.6% to 1.8% of a carboxymethyl cellulose (CMC) by weight of the oral composition. In yet another embodiment, the aforementioned thickener further comprises 0.5% to 5%, preferably 1% to 4%, of a thickening silica by weight of the oral composition.

Low or Free Humectants

The oral compositions herein may be substantially free or free of humectants, or alternatively contain low levels of humectants. The term "humectant," for the present invention, includes edible polyhydric alcohols such as glycerin, sorbitol, xylitol, butylene glycol, propylene glycol, and combinations thereof. In one embodiment, the humectant is selected from glycerin, sorbitol, xylitol, butylenes glycol, polyethylene glycol, propylene glycol and combinations thereof. In yet another embodiment, the humectant is sorbitol. In one embodiment, the oral composition comprises from 0% to less than 20% of humectants by weight of the oral composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the oral composition. In yet another embodiment, the oral composition contains less than 20% of sorbitol by weight of the oral composition.

In an alternative embodiment, the oral compositions of the present invention comprise a humectant, preferably from 1% to 15% by weight of the oral composition.

Colorant

The oral compositions herein may include a colorant. Titanium dioxide is one example of a colorant. Titanium dioxide is a white powder which adds opacity to the compositions. Titanium dioxide generally can comprise from about 0.25% to about 5%, by weight of the oral composition.

Flavorant

The oral compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the oral composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Anti-Microbial Active

The present invention may also include an antimicrobial active. Water insoluble non-cationic antimicrobial actives and water soluble antimicrobial actives such as quaternary ammonium salts and bis-biquanide salts are suitable for inclusion among others. Triclosan monophosphate is an additional water soluble antimicrobial active. In some preferred embodiments, the antimicrobial active is selected from the group consisting of cetylpyridinium halide, domiphen halide, stannous ion source, zinc ion source, copper ion source, and combinations thereof. These antimicrobial actives may be present at levels of from 0.01%, 0.05%, 0.1%, or 0.2% to 0.5%, 1.0%, 1.2% or 1.5% by weight.

The Method and Use

The present invention also relates to a method of controlling dental calculus or tartar, comprising the step of administering to a subject's oral cavity an oral composition of the present invention.

In a specific embodiment, the method comprises the step of contacting the oral composition of the present invention with the subject's teeth for more than 1 second, preferably more than 5 seconds, more preferably more than 10 seconds, or most preferably more than 30 seconds. The benefits of the present oral composition may increase over time when the oral composition is used repeatedly.

The subject may be any human or animal whose tooth surface and oral cavity need to be treated with the present oral composition. "Animal" is meant to include household pets or other domestic animals, or animals kept in captivity.

The present invention further relates to the use of a calcium-catching phosphate source for manufacturing an anti-calculus oral composition, wherein the anti-calculus oral composition comprises a calcium-containing abrasive and has a pH from 8 to 11, and wherein the calcium-catching phosphate source is present in an amount sufficient to provide at least 100 mM of phosphate ions, $PO_4^{3-}$, in the anti-calculus oral composition.

EXAMPLES

The examples herein are meant to exemplify the present invention but are not used to limit or otherwise define the scope of the present invention.

Oral Compositions

Oral compositions according to the present invention are shown in Table 1. Comparative oral compositions are shown in Table 2. All ingredient amounts are described in weight percentage (wt %) unless otherwise indicated. The oral compositions are prepared as follows: add water and water soluble salts to a main mixing tank, mixing well and ensuring all the salts have dissolved; add thickening agents and/or pyrophosphate into the main mixing tank, mixing/homogenizing until well dispersed and homogeneous; add sodium lauryl sulfate solution, flavors and coloring agents to the main mixing tank, mixing until homogeneous; and cool batch to less than 35° C.

Efficacy Measurement

Two measurement methods are used to demonstrate and compare the efficacy of the anti-calculus performance. The Crystal Growth Inhibition (CGI) test is an in-vitro calculus inhibition test method while the Modified Plaque Growth and Mineralization Model (mPGM) is a methodology correlated to clinical calculus reduction results.

(A) Crystal Growth Inhibition (CGI) Test

The CGI test is designed to examine mineral growth or dissolution kinetics under constant solution pH. The CGI test involves the following steps:
1) 25% wt/wt composition slurry is prepared and centrifuged at 10,000 rpm for 15 minutes.
2) 10 grams supernatant is placed in a clean test tube.

TABLE 1

Oral Compositions of the Present Invention

| INGREDIENTS | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Tetra Sodium Pyrophosphate | 2.0 | 3.0 | 5.1 | 5.1 | 5.1 | 7.6 | 2.0 | — | — | — |
| Disodium Acid Pyrophosphate | — | — | — | — | — | — | — | — | — | — |
| Sodium Tripolyphosphate | — | — | — | — | — | — | — | 1.8 | — | — |
| Sodium Polyphosphate | — | — | — | — | — | — | — | — | 2.2 | — |
| Phytic Acid | — | — | — | — | — | — | — | — | — | 2.3 |
| Carrageenan | 1.3 | 1.3 | 1.5 | 1.3 | 0.8 | 1.3 | 1.3 | 1.3 | 1.3 | 1.3 |
| Sodium Carboxymethyl Cellulose | 1.0 | 1.0 | 1.0 | 1.0 | 1.0 | 1.0 | 1.0 | 1.0 | 1.0 | 1.0 |
| Benzyl alcohol | 0.3 | 0.3 | 0.3 | 0.3 | 0.3 | 0.3 | 0.3 | 0.3 | 0.3 | 0.30 |
| Methylparaben, NF | 0.15 | 0.15 | 0.15 | 0.15 | 0.15 | 0.15 | 0.15 | 0.15 | 0.15 | 0.15 |
| Prophlparaben, NF | 0.05 | 0.05 | 0.05 | 0.05 | 0.05 | 0.05 | 0.05 | 0.05 | 0.05 | 0.05 |
| Zeodent 165 | 3.0 | 3.0 | 3.0 | 3.0 | 3.0 | 3.0 | 3.0 | 3.0 | 3.0 | 3.0 |
| Sodium Saccharin | 0.3 | 0.3 | 0.3 | 0.3 | 0.3 | 0.3 | 0.3 | 0.3 | 0.3 | 0.3 |
| Sodium Monofluorophosphate | 1.1 | 1.1 | 1.1 | 1.1 | 1.1 | 1.1 | 1.1 | 1.1 | 1.1 | 1.1 |
| Sodium Monophosphate | 0.1 | 0.1 | 0.1 | 0.1 | 0.1 | 0.1 | 0.1 | 0.1 | 0.1 | 0.1 |
| Sodium Triphosphate | 0.5 | 0.5 | 0.5 | 0.5 | 0.5 | 0.5 | 0.5 | 0.5 | 0.5 | 0.5 |
| Calcium Carbonate | 32 | 32 | 20 | 32 | 50 | 32 | 32 | 32 | 32 | 32 |
| Sodium Lauryl Sulfate | 1.3 | 1.3 | 1.3 | 1.3 | 1.3 | 1.3 | 1.3 | 1.3 | 1.3 | 1.3 |
| Flavor | 1.0 | 1.0 | 1.0 | 1.0 | 1.0 | 1.0 | 1.0 | 1.0 | 1.0 | 1.0 |
| Sorbitol | — | — | — | — | — | — | 17 | — | — | — |
| Deionized Water | 55.9 | 54.9 | 64.6 | 52.8 | 35.3 | 50.3 | 38.9 | 56.1 | 55.7 | 55.6 |
| Total | 100.0 | 100.0 | 100.0 | 100.0 | 100.0 | 100.0 | 100.0 | 100.0 | 100.0 | 100.0 |

TABLE 2

Comparative Oral Compositions

| INGREDIENTS | Com. Ex. 1 | Com. Ex. 2 | Com. Ex. 3 | Com. Ex. 4 | Com. Ex. 5 | Com. Ex. 6 |
|---|---|---|---|---|---|---|
| Sorbitol | — | — | — | — | 30 | 30 |
| Silica | — | — | — | — | 20 | 20 |
| Calcium Carbonate | 32 | 32 | 32 | 32 | — | — |
| Sodium Fluoride | — | — | — | — | 0.32 | 0.32 |
| Sodium Monofluorophosphate | 1.1 | 1.1 | 1.1 | 1.1 | — | — |
| Tetra Sodium Pyrophosphate | — | 0.7 | 0.9 | — | — | 3.3 |
| Disodium Acid Pyrophosphate | — | — | — | 1.65 | 3.19 | — |
| Sodium Monophosphate | 0.1 | 0.1 | 0.1 | 1.0 | — | — |
| Sodium Triphosphate | 0.5 | 0.5 | 0.5 | — | — | — |
| Sodium Carboxymethyl Cellulose | 1.0 | 1.0 | 1.0 | 1.0 | 1.0 | 1.0 |
| X-gum | — | — | — | — | 0.5 | 0.5 |
| Carrageenan | 1.3 | 1.3 | 1.3 | 1.3 | — | — |
| Sodium Lauryl Sulfate | 1.3 | 1.3 | 1.3 | 1.3 | 2.1 | 2.1 |
| Sodium Saccharin | 0.3 | 0.3 | 0.3 | 0.3 | 0.3 | 0.3 |
| Flavor | 1.0 | 1.0 | 1.0 | 1.0 | 1.0 | 1.0 |
| Benzyl alcohol | 0.3 | 0.3 | 0.3 | 0.3 | — | — |
| Methylparaben, NF | 0.15 | 0.15 | 0.15 | 0.15 | — | — |
| Prophlparaben, NF | 0.05 | 0.05 | 0.05 | 0.05 | — | — |
| Zeodent 165 | 3.0 | 3.0 | 3.0 | 3.0 | — | — |
| Deionized Water | 57.9 | 57.13 | 56.9 | 55.25 | 41.59 | 41.48 |
| Total | 100.0 | 100.0 | 100.0 | 100.0 | 100.0 | 100.0 |

3) 3 ml of a hydroxyapatite (HAP) slurry (about 0.3 g) is added to the supernatant and mixed for 1 minute.
4) 20 g of water is added into the tube to "quench" the reaction.
5) The treatment mixture is centrifuged at 10,000 rpm for 15 minutes and the fluid is decanted.
6) The HAP plug is washed twice by resuspending in 30 mL of water and centrifuged at 10,000 rpm for 15 minutes.
7) The resultant HAP plug is dried in a test tube at 37° C. for 24 hours or until dry.
8) The seed is ground using a mortar and pestal.
9) 0.050 g of the treated HAP seed is weighed out and injected into a reaction vessel containing 50 mL artificial saliva (1.75 mM calcium, 1.05 mM phosphate and 0.15 M NaCl).
10) The rates of crystal growth are compared against non-inhibited growth curves.

All of the freshly prepared compositions except Comparative Example 6 are tested and the results are shown in Table 3.

TABLE 3

CGI values of freshly prepared compositions

| | $PO_4^{3-}$ (mM) | Soluble $P_2O_7^{4-}$ (ppm) | pH | CGI |
|---|---|---|---|---|
| Ex. 1 | 146 | 800 | 9.9 | 36.6 |
| Ex. 2 | 219 | 1000 | 10 | 23.1 |
| Ex. 3 | 371 | 1100 | 10.1 | 43.0 |
| Ex. 4 | 371 | 1300 | 10.1 | 43.2 |
| Ex. 5 | 371 | 1300 | 10.1 | 44.9 |
| Ex. 6 | 553 | 1500 | 10.4 | 43.1 |
| Ex. 7 | 146 | 1200 | 9.7 | 21.6 |
| Ex. 8 | 146 | —* | 9.4 | 33.2 |
| Ex. 9 | 146 | —* | 9.1 | 33.8 |
| Ex. 10 | 146 | —* | 9.3 | 40.2 |
| Com. Ex. 1 | 0 | 0 | 8.5 | 0 |
| Com. Ex. 2 | 51 | 500 | 9.3 | 7.0 |
| Com. Ex. 3 | 66 | 700 | 9.6 | 7.2 |
| Com. Ex. 4 | 146 | 1100 | 6.7 | 3.3 |
| Com. Ex. 5 | 287 | 7000 | 7.6 | 31.2 |
| Com. Ex. 6 | 240 | 7000 | 7.6 | —* |

*not tested.

From table 3, it can be seen that all freshly prepared compositions according to the present invention provide good inhibition of calculus formation via CGI test. $PO_4^{3-}$ can be from various sources, for example, tetra sodium pyrophosphate (as in Ex. 1 to Ex. 7), sodium tripolyphosphate (as in Ex. 8), sodium polyphosphate (as in Ex. 9), and phytic acid (as in Ex. 10). The data for Examples 3 to 5 show that the present invention applies to a broad $CaCO_3$ range.

The CGI values of Examples 1 to 10 according to the present invention are significantly higher than those of Comparative Examples 1 to 4. Each of Comparative Examples 1 to 4 is an oral composition with calcium carbonate as an abrasive. Comparative Example 1 does not comprise a calcium-catching phosphate source. Comparative Examples 2 and 3 each has a molar concentration of phosphate ions, $PO_4^{3-}$, of less than 100 mM. Comparative Example 4 has a pH of 7.6 which is below the pH range as required by the present invention.

The CGI values of Examples 1 to 10 according to the present invention can be the same as or even higher than those of Comparative Example 5. Comparative Example 5 is an oral composition with silica as an abrasive and disodium acid pyrophosphate as an anticalculus agent which has been clinically proven to be effective in controlling dental calculus. As shown in Table 3, the oral composition of Comparative Example 5 has a much higher level of soluble pyrophosphaste ions ($P_2O_7^{4-}$) than the oral composition according to the present invention. Previously, it was believed that the anticalculus benefit was achieved because of the presence of soluble $P_2O_7^{4-}$ in the oral composition. The higher the concentration of the soluble $P_2O_7^{4-}$ is, the more anticalculus benefit the oral composition can provide. However, the present inventors surprisingly found that, although the present oral composition has a very low concentration of soluble $P_2O_7^{4-}$, comparable efficacy of inhibiting crystal growth and calculus formation can be achieved.

To demonstrate the storage stability of the composition in terms of the anticalculus efficacy, the composition of Ex. 2 was loaded into plastic laminated tubes, sealed and then aged at 25° C. for 12 weeks. The CGI value of Ex. 2 after aging is 20.2, which is almost same as that before aging (e.g., 23.1 as shown in Table 3).

(B) Modified Plaque Growth and Mineralization Model (mPGM) Test

Modified Plaque Growth and Mineralization Model (mPGM) is a technique in which plaque is grown from human saliva under conditions designed to promote its mineralization.

The purpose of this technique is to: 1) define the tartar efficacy of a compound; 2) examine the kinetics of inhibitor reactions; and 3) define the mechanism of a tartar active. The protocol for this method is as follows:

1) Glass rods with one end roughened by 600 grit silicon carbide paper are used as a matrix to grow plaque. The glass rods are dipped in human saliva and the plaque are grown in growth media at 37° C. for the first 4 days.
2) Once the plaque has formed on the end of the glass rods, the end of the rods are treated with a dentifrice slurry by dipping them in the slurry for 30 seconds and then washed 2 times for 10 seconds each by dipping them in test tubes containing DI water, to remove all traces of the dentifrice. The end of the rods with the plaque are placed in a mineralization solution for 6 hours each day and then stored overnight in human saliva. This procedure is repeated for 6 days.
3) The plaque is air dried and dissolved with 0.9 M KOH solution, then 1M HCl:1M HAc solution.
4) The level of calcium in solution is measured with Inductively Coupled Plasma Optical Emission Spectrometry (ICP-OES) at 317.933 nm. Calcium standards are prepared at concentrations of 5, 10, 25, 50, 100, and 200 ppm in a 2:1 0.9M KOH/1MHCl:1M HAc matrix.
5) Results are reported as mean mg calcium, and mg calcium per mg dry deposit weight. Final results are reported as percent reduction of mg calcium versus negative control (or percent reduction of mg calcium per mg dry deposit weight if plaque growth is uneven due to excessive scraping or fall off).
6) Example 2 and Comparative Examples 1, 2, 5 and 6 are tested by mPGM and the results are shown in Table 4. The mPGM value is essentially consistent with the CGI value. Based on the mPGM value, the present oral composition (Ex. 2) provides significantly better anti-calculus efficacy than the compositions of Comparative Examples 1 and 2, and comparable anti-calculus efficacy to the compositions of Comparative Examples 5 and 6.

TABLE 4 mPGM values of freshly prepared compositions

| | mPGM |
|---|---|
| Ex. 2 | 24 |
| Com. Ex. 1 | 0 |
| Com. Ex. 2 | 2.28 |
| Com. Ex. 5 | 34 |
| Com. Ex. 6 | 20 |

Unless otherwise indicated, all percentages, ratios, and proportions are calculated based on weight of the total composition. All temperatures are in degrees Celsius (° C.) unless otherwise indicated. All measurements made are at 25° C., unless otherwise designated. All component or composition levels are in reference to the active level of that component or composition, and are exclusive of impurities, for example, residual solvents or by-products, which may be present in commercially available sources.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral composition comprising:
   (a) from 20 wt % to 60 wt % of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite and combinations thereof;
   (b) a pyrophosphate source in an amount sufficient to provide at least 200 mM of phosphate ions, $PO_4^{3-}$;
   (c) no more than 20 wt % of a humectant; and
   (d) from 30 wt % to 60 wt % of water;
   wherein the pyrophosphate source is selected from the group consisting of dialkali metal pyrophosphate salts, tetraalkali metal pyrophosphate salts, and combinations thereof;
   wherein the composition is substantially free of a humectant selected from the group consisting of glycerin, sorbitol, xylitol, and combinations thereof; and
   wherein the oral composition has a pH from 9.5 to 11.

2. The oral composition according to claim 1, wherein the calcium-containing abrasive is selected from the group consisting of fine ground natural chalk, ground calcium carbonate, precipitated calcium carbonate and combinations thereof.

3. The oral composition according to claim 1, wherein the pyrophosphate source comprises tetrasodium pyrophosphate.

4. The oral composition according to claim 1, wherein the pyrophosphate source is present in an amount sufficient to provide from 200 mM to 1,000 mM of phosphate ions, $PO_4^{3-}$.

5. The oral composition according to claim 4, wherein the pyrophosphate source is present in an amount sufficient to provide from 300 mM to 600 mM $PO_4^{3-}$.

6. The oral composition according to claim 1, wherein the composition is free of the humectant.

7. The oral composition according to claim 1, wherein the composition is substantially free of edible polyhydric alcohols.

8. The oral composition according to claim 1, wherein the water is present in an amount from 40 wt % to 60 wt %.

9. The oral composition according to claim 1, wherein the oral composition has a pH from 9.5 to 10.7.

10. The oral composition according to claim 1, wherein the calcium-containing abrasive is present in an amount of from 20 wt % to 50 wt %.

11. The oral composition according to claim 1, further comprising sodium monofluorophosphate.

12. The oral composition according to claim 1, further comprising a thickening agent selected from the group consisting of xanthan gum, cellulosic polymer, carrageenan, polyacrylic acid, cross-linked polyacrylic acid, polycarbophil, alginate, clay, glucose, pectin, gelatin and combinations thereof; and wherein the thickening agent is present in an amount from 0.01 wt % to 20 wt %.

13. The oral composition according to claim 12, wherein the thickening agent is present in an amount from 0.3 wt % to 3 wt %.

14. The oral composition according to claim 1, further comprising an anti-microbial active selected from the group consisting of cetylpyridinium halide, domiphen halide, stannous ion source, zinc ion source, copper ion source and combinations thereof.

15. An oral composition comprising
   (a) 20 wt % to 60 wt % calcium-containing abrasive selected from the group consisting of fine ground natural chalk, ground calcium carbonate, precipitated calcium carbonate and combinations thereof;
   (b) at least 3 wt % tetrasodium pyrophosphate wherein the tetrasodium pyrpophosphate is present in an amount sufficient to provide from 300 mM to 600 mM $PO_4^{3-}$;

(c) 40 wt % to 60 wt % water;
(d) wherein the oral composition has a pH from 9.5 to 11; and
wherein the oral composition further comprises sodium monofluorophosphate;
wherein the composition is substantially free of a humectant selected from the group consisting of glycerin, sorbitol, xylitol, and combinations thereof; and
wherein oral composition is a dentifrice.

16. The oral composition according to claim 15, wherein the composition is free of the humectant.

17. An oral composition comprising:
(e) from 20 wt % to 60 wt % of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite and combinations thereof;
(f) a pyrophosphate source in an amount sufficient to provide at least 200 mM of phosphate ions, $PO_4^{3-}$;
(g) no more than 20 wt % of a humectant; and
(h) from 30 wt % to 60 wt % of water;
wherein the pyrophosphate source is selected from the group consisting of dialkali metal pyrophosphate salts, tetraalkali metal pyrophosphate salts, and combinations thereof;
wherein the composition is substantially free of a humectant selected from the group consisting of glycerin, sorbitol, xylitol, and combinations thereof;
wherein the oral composition has a pH from 9 to 11.

* * * * *